United States Patent [19]

Henderson et al.

[11] 4,386,211

[45] May 31, 1983

[54] ANTI-ULCER UREA COMPOUNDS

[75] Inventors: Richard E. L. Henderson, Evanston; Barnett S. Pitzele, Skokie, both of Ill.

[73] Assignee: G. D. Searle & Co., Skokie, Ill.

[21] Appl. No.: 295,986

[22] Filed: Aug. 25, 1981

[51] Int. Cl.³ ............................................. C07D 417/12
[52] U.S. Cl. ................................. 548/196; 548/214; 548/336; 548/163; 424/270; 424/273 R
[58] Field of Search ................................ 548/196

[56] References Cited

U.S. PATENT DOCUMENTS

Re. 27,506 10/1972 Guillot et al. .................. 548/196
3,734,923 5/1973 Dowding et al. ............... 548/196

*Primary Examiner*—Robert Gerstl
*Attorney, Agent, or Firm*—James G. Passe

[57] ABSTRACT

The invention relates to certain urea derivatives of the formula $R_1CH_2S(CH_2)_2NHCONHR_2$ where $R_1$ are certain furanyls, imidazoles and thiazolyls and $R_2$ are certain imidazoles and thiazolyls. These compounds are H-2 histamine receptor inhibitors and therefore useful in the treatment of ulcers.

4 Claims, No Drawings

ANTI-ULCER UREA COMPOUNDS

BACKGROUND OF THE INVENTION

The invention relates to novel urea compounds. In particular it relates to novel urea compounds of the formula $R_1CH_2S(CH_2)_2NHCONHR_2$, which are inhibitors of H-2 histamine receptors and, therefore, useful as anti-ulcer agents.

It has long been postulated that many of the physiologically active substances within the animal body, in the course of their activity, combine with certain specific sites known as receptors. Histamine is a compound which is believed to act in such a way, but since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated as H-1. A further group of substances has been described by Black et al. (Nature 1974, 236, 385) which are distinguished by the fact that they act at histamine receptors other than the H-1 receptor and these receptors have been designated as H-2 receptors. This latter group of substances, to certain of which the present invention relates, are thus of utility in inhibiting certain actions of histamines which are not inhibited by the above-mentioned "antihistamines;" that is, they are H-2 histamine receptor inhibitors. Inhibitors of H-2 histamine receptors, which are also referred to as histamine H-2 antagonists, are useful, for example, as inhibitors of gastric acid secretion. The histamine H-2 antagonists of this invention may also be of utility as inhibitors of certain actions of gastrin. In the treatment of certain conditions, for example inflammation and in inhibiting the actions of histamine, H-1 and H-2 antagonists are useful.

PRIOR ART

Cimetidine is the H-2-receptor antagonist currently available for treatment of patients with duodenal ulcer and massive gastric acid hypersecretion. While no severe toxic symptoms appear in humans, the following untoward effects have been observed with cimetidine: gynecomastia, elevated SGOT, SGPT and creatine, and increases in serum gastrin; see Cecil, Textbooks of Medicine, pp. 1514-1515 (1979). U.S. Pat. No. 4,025,527, Durant et. al., discloses N,N' substituted thioureas, ureas and guanidine which are H-2 histamine inhibitors.

SUMMARY OF THE INVENTION

A compound according to the formula;
$R_1CH_2S(CH_2)_2NHCONHR_2$
wherein
  $R_1$ is:
  (a) 5-[di(loweralkyl)aminomethyl]-2-furanyl
  (b) 5-methyl-1H-imidazol-4-yl
  (c) 2-[(aminoiminomethyl)amino]-4-thiazolyl
wherein
  $R_2$ is:
  (a) 2-benzothiazolyl
  (b) 4-methyl-2-thiazolyl
  (c) 1H-imidazol-2-yl
  (d) 3-methyl-5-isothiazolyl Examples of lower alkyl are, alkyls from 1 to 6 carbon atoms inclusive, such as methyl, ethyl, propyl, butyl, pentyl and hexyl, and the isomeric forms thereof.

The tests used to determine anti-ulcer activity are as follows:

I Lipolysis Assay

Isolated fat cells of dogs are prepared from adipose tissue. Cells are incubated in the presence or absence of histamine at $2\times10^{-6}$ M. Additional flasks contain the compound to be tested, plus histamine. At the end of the incubation the cell cultures are analyzed for glycerol content, and results are converted into a lipolysis rate. The stimulation of lipolysis attributed to histamine (D) is the difference between the rate observed in its presence and absence:

$$D = R_{(+H)} - R_{(-H)}.$$

The effects of a compound on lipolysis (E), where E is the difference and rate observed with the test compound in the presence of histamine ($R_u$) and the control rate is expressed by:

$$E = R_u - R_{(-H)}.$$

These figures are then converted to a percent inhibition by the formula:

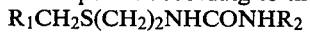

Percent inhibition $=(D-E)/D\times 100$

A compound is considered active if it exhibits 50 percent or more inhibition at the screening dose. If E is greater than D, then the compound potentiates the effect of histamine and is a potential agonist. If the compound is rated active, it is later tested for its efffect on norepinephrine—stimulated lipolysis in the same manner. A compound active against histamine but not norepinephrine is termed a specific H₂ receptor antagonist. A compound active against both histamine and norepinephrine is termed a nonspecific lipolysis inhibitor.

The basis of test I is that the known H₂-blockers metiamide and cimetidine are both specific inhibitors in the system. A good correlation exists between compounds that are specific H-2 receptor antagonists and this assay and their activity in the rat uterus assay.

II Rat Uterus Assay

Histamine reduces contractions induced by electrical stimulation of the isolated rat uterine smooth muscle, and histamine H-2 antagonists reverse this inhibition. The dose ratio for a specific concentration of test compound is determined by an assay procedure that compares the inhibitory effect of two concentrations of histamine in the presence of the test compound to the inhibitory effect of two concentrations of histamine in the absence of the test compound. The dose ratio is defined as the ratio of the concentration of histamine in the presence of the test compound to the concentration of histamine in the absence of the test compound where both concentrations produce the same inhibition of the electrical response. Dose ratios of 2 or more indicate activity. Compounds that are active at 40 ug/ml will be tested against isoproterenol at the same concentration in a similar test. Compound concentrations that are active against histamine but not against isoproterenol will be classified as specific H-2 antagonists.

The same type of receptors H-2 are involved in inhibition of contractions of the rat uterus and stimulation of gastric acid secretion. The rat uterus is therefore used as a model upon which to test for histamine H-2 antagonists that may be effective in treating peptic ulcers.

The H-2 antagonists burimamide, metiamide and cimetidine are active in this test and they also inhibit gastric acid secretion and ulcer formation.

By virtue of their anti-ulcer activity, the compounds of the present invention are useful in treating ulcers in humans and animals. A physician or veterinarian of ordinary skill could readily determine a subject who is exhibiting ulcer symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, solutions, suspentions or granules. They also may be administered rectally or vaginally in such forms as creams, ointments, gels, suppositories or bougies; they may also be introduced in the form of eye drops, interparenterally, subcutaneously, or intramuscularly, using forms known to the pharmaceutical art. In general, the preferred form of administration is orally.

An effective but non-toxic quantity of the compound is employed in treatment. The dosage regimen for preventing or treating ulcers by the compounds of this invention is selected in accordance with a variety of factors including the type, age, weight, sex, and medical condition of the mammal, the severity of the ulcers, the route of administration and the particular compound employed. An ordinarily skilled physician or veterinarian will readily determine and prescribe the effective amount of the anti-ulcer agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 3 mg/kg up to at least 100 mg/kg orally. When other forms of administration are employed equivalent doese are administered. When dosages beyond 100 mg/kg are employed, care should be taken with each subsequent dosage to monitor possible effects.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of the present invention may be prepared by the following method.

An aromatic amine is converted to the corresponding alkoxycarbonylamino compound by reaction in a suitable solvent with a lower alkyl chloroformate in the presence of a base, which may be the solvent itself, or with a dialkyl pyrocarbonate (or, dialkyl dicarbonate; alkoxyformic anhydride). For those aryl amines which multiply acylate (as on a ring nitrogen) acid hydrolysis of the intermediate mixture, followed by neutralization, affords the desired singly acylated compound.

A heterocyclic-substituted alkylamine, or a salt thereof, and an alkoxycarbonylamino compound are stirred in refluxing pyridine to obtain the desired urea product. (When employing an aralkylamine salt, the free base should first be liberated by addition of an alkali metal hydride to a room-temperature mixture of the salt in pyridine.) Purification by column chromatography affords analytically pure product.

DESCRIPTION OF THE PREFERRED EMBODIMENTS

The operation of this invention is further elaborated by the representative examples below:

EXAMPLE 1

2-carbethoxyamino-4-methylthiazole

A mixture of 5.00 g (43.8 mmole) of 2-amino-4-methylthiazole and 21.0 g (130 mmole) of diethyl pyrocarbonate is stirred in 100 ml of dimethylformamide, with provision for evolution of carbon dioxide. After 18 hours the reaction mixture is treated with 10 ml each of water and ethanol and stirred for approximately 1 hour, then concentrated at reduced pressure to a gum. Addition and evaporation of several quantities of aqueous ethanol produce a sticky solid. The crude product is dissolved in less than 75 ml of hot ethanol and filtered. About 30 to 40 ml of water is added to the filtrate, which is then concentrated by boiling until the volume is reduced to about 75 ml. From the cooled solution is precipitated 7.27 g (39.0 mmole) of analytically pure yellow crystals of the product. Structure assignment is supported by the nmr spectrum.

Analysis: Calculated for $C_7H_{10}N_2O_2S$: C, 45.15; H, 5.41; N, 15.04; S, 17.22. Found: C, 45.08; H, 5.36; N, 15.27; S, 17.32.

A second crop of less pure product can be isolated from the mother liquors.

EXAMPLE 2

2-carbethoxyaminothiazole

To a stirred solution of 15.1 g (151 mmole) of 2-aminothiazole in 200 ml of dry pyridine is added slowly 18.8 g (173 mmole) of ethyl chloroformate. After approximately 1 day, insolubles are removed by filtration and discarded and the filtrate is concentrated at reduced pressure. The resultant gum is dissolved in aqueous ethanol and redried $in\ vacuo$ to a sticky solid. The crude product is dissolved in a boiling mixture of 100 ml of ethanol and 25 ml of water, clarified by filtration, and allowed to cool. The resultant crystalline solid is collected and washed thoroughly with water, giving 11.3 g (65.6 mmole) of 2-carbethoxyaminothiazole as a tlc-homogeneous (ethyl acetate eluent on silica gel plates) substance. Structure assignment is supported by the nmr spectrum.

A second crop of slightly less pure material is isolated from the mother liquors.

EXAMPLE 3

5-carbethoxyamino-3-methylisothiazole

To a stirred solution of 6.10 g (40.5 mmole) of 5-amino-3-methylisothiazole hydrochloride in 200 ml of dry pyridine is added slowly 13.8 g (127 mmole) of ethyl chloroformate. After 2 days the reaction mixture is treated with 20 ml each of water and ethanol. After 40 min., the solution is concentrated $in\ vacuo$ to a gum, which is further dried by several evaporations of aqueous ethanol. The crude product is dissolved in 75 ml of boiling ethanol to which is added water until the solution clouds. Upon cooling a crystaline solid containing some diacylated material is collected, redissolved in 100 ml of isopropyl alcohol, and treated with 40 ml of approximately 7 N HCl in isopropyl alcohol. After about 2 hours, the solution is concentrated at reduced pressure to an oily residue which is dried by multiple evaporation of ethanol. A solution of the crude solid in approximately 100 ml of water is adjusted to about pH 7 by addition of 2 N aqueous sodium hydroxide, giving the product as a precipitate. After washing with water and drying, 4.71 g (25.3 mmole) of 5-carbethoxyamino-3-methylisothiazole is obtained. Structure assignment is supported by the nmr spectrum.

EXAMPLE 4

N-[2-[[2-[(aminoiminomethyl)amino]-4-thiazolyl]methylthio]ethyl]-N'-(4-methyl-2-thiazolyl)urea To 4.60 g (15.1 mmole) of 2-guanidino-4-[(2-aminoethyl)thiomethyl]thiazole dihydrochloride stirred under flowing nitrogen in 170 ml of dry pyridine is added 1.38 g (ca. 30.3 mmole) of a 50 percent dispersion in oil of sodium hydride. After about 1 hour 2.80 g (15.0 mmole) of 2-carbethoxyamino-4-methylthiazole is added, and the resultant mixture is heated at reflux for 2 days. After partial cooling, the mixture is decanted through a sintered glass funnel using suction, all residues being discarded, and the filtered supernatant is concentrated in vacuo to a thick gum. Residual mineral oil is removed by trituration with several portions of diethyl ether and pentane, and the residue is purified by column chromatography* on silica gel. Fractions containing the product are combined, partially concentrated, filtered, and thoroughly dried by concentration *in vacuo*, giving 1.20 g (3.1 mmole) of the desired product as an ethanol solvate. Structure assignment and solvation by one quarter mole of ethanol per mole of product are supported by nmr.

*Elution using 85:15:0.5 $CH_2Cl_2$/EtOH/conc.$NH_4OH$

Analysis: Calculated for $C_{12}H_{17}N_7OS_3.\frac{1}{4}$ EtOH: C, 39.20; H, 4.87; N, 25.60; S, 25.11. Found: C, 39.15; H, 4.61; N, 25.69; S, 25.09.

EXAMPLE 5

N-[2-[(5-methyl-1H-imidazol-4-yl)methylthio]ethyl]-N'-(4-methyl-2-thiazolyl)urea To 3.40 g (13.9 mmole) of 4-[(2-aminoethyl)thiomethyl]-5-methylimidazole dihydrochloride stirred under flowing nitrogen in 100 ml of dry pyridine is added 1.27 g (ca. 27.9 mmole) of a 50 percent dispersion in oil of sodium hydride. After approximately 90 min. 24.3 g (13.1 mmole) of 2-carbethoxyamino-4-methylthiazole is added, and the resultant mixture is heated at reflux for 1 day. After cooling to room temperature, the mixture is filtered to remove insolubles, and the filtrate is concentrated at reduced pressure. The resultant gum is repeatedly dissolved in aqueous ethanol and dried *in vacuo*, triturated with pentane to remove mineral oil, and purified by column chromatography* on silica gel. Fractions containing the product are combined, partially concentrated, filtered and finally dried by concentration *in vacuo*, giving 2.40 g (7.2 mmole) of the desired product as an ethanol solvate. Structure assignment and solvation by one-half mole of ethanol per mole of product are supported by nmr.

*Elution using 90:1-:0.5 $CH_2Cl_2$/EtOH/conc. $NH_4OH$

Analysis: Calculated for $C_{12}H_{17}N_5OS_2.\frac{1}{2}$ EtOH: C, 46.68; H, 6.03; N, 20.94; S, 19.17. Found: C, 47.09; H, 5.80; N, 21.07; S, 19.05.

EXAMPLE 6

N-[2-[(5-methyl-1H-imidazol-4-yl)methylthio]ethyl]-N'-(1H-imidazol-2-yl)urea

The compound is prepared according to the method of Example 5 using 5.50 g (22.5 mmole) of 4-[2-aminoethyl)thiomethyl]-5-methylimidazole dihydrochloride and 2.05 g (45.0 mmole) of sodium hydride in oil in 100 ml of pyridine; and 3.38 g (21.8 mmole) of 2-carbethoxyaminoimidazole, prepared from 2-aminoimidazole according to the method of Example 3. Chromatography and crystallization from ethanol affords the desired compound (0.97 g, 3.4 mmole) as an ethanol solvate. Structure assignment and solvation by one-eighth mole of ethanol per mole of product are supported by nmr.

Analysis: Calculated for $C_{11}H_{16}N_6OS.\frac{1}{8}$ EtOH: C, 47.23; H, 5.90; N, 29.37; S, 11.21. Found: C, 47.21; H, 5.77; N, 29.20; S, 11.56.

EXAMPLE 7

N-[2-[(5-methyl-1H-imidazol-4-yl)methylthio]ethyl]-N'-(2-benzothiazolyl)urea

The compound is prepared according to the method of Example 5 using 6.12 g (25.1 mmole) of 4-[(2-aminoethyl)thiomethyl]-5-methylimidazole dihydrochloride, and 2.29 g (50.2 mmole) of sodium hydride in oil in 100 ml of pyridine and 5.55 g (25.0 mmole) of 2-carbethoxyaminobenzothiazole, prepared from 2-aminobenzothiazole according to the method of Example 2. Chromatography, followed by trituration with pentane, affords the desired compound (1.43 g, 4.1 mmole). Structure assignment is supported by nmr.

Analysis: Calculated for $C_{15}H_{17}N_5OS_2$: C, 51.85; H, 4.93; N, 20.16; S, 18.46. Found: C, 52.00; H, 4.97; N, 19.74; S, 18.37.

EXAMPLE 8

N-[2[[(dimethylamino)methyl]-2-furanyl]methylthio]-N'(4-methyl-2-thiazolyl)urea

The compound is prepared according to the method of Example 5 using 4.32 g (20.2 mmole) of 2-[(aminoethyl)thiomethyl]-5-(dimethylaminomethyl)furan and 3.70 g (19.9 mmole) of 2-carbethoxyamino-4-methythiazole (Ex. 1) in 100 ml of pyridine, but without sodium hydride. Chromatography, followed by trituration with pentane, affords the desired compound (3.64 g, 10.3 mmole). Structure assignment is supported by nmr.

Analysis: Calculated for $C_{15}H_{22}N_4O_2S_2$: C, 50.82; H, 6.26; N, 15.81; S, 18.09. Found: C, 50.70; H, 6.18; N, 15.59; S, 18.20.

EXAMPLE 9

N-[2-[[5-(dimethylamino)methyl]-2-furanyl]methylthio]-N'-(3-methyl-5-isothiazolyl)urea The compound is prepared according to the method of Example 5 using 3.25 g (15.2 mmole) of 2-[(aminoethyl)thiomethyl]-5-(dimethylamino-methyl)furan and 2.79 g (15.0 mmole) in 75 ml of pyridine, but without sodium hydride. Chromatography, followed by trituration with pentane, affords the desired compound (2.30 g, 6.5 mmole). Structure assignment is supported by nmr.

Analysis: Calculated for $C_{15}H_{22}N_4O_2S_2$: C, 50.82; H, 6.26; N, 15.81; S, 18.09. Found: C, 50.49; H, 6.13; N, 15.64; S, 18.02.

We claim:
1. A compound of the formula

R₁CH₂S(CH₂)₂NHCONHR₂ wherein
R₁ is:
(a) 5-[di(loweralkyl)aminomethyl]-2-furanyl
(b) 5-methyl-1H-imidazol-4-yl
(c) 2-[(aminoiminomethyl)amino]-4-thiazolyl
wherein
R₂ is:
(a) 4-methyl-2-thiazolyl 2. N-[2-[[2-[(aminoiminomethyl)amino]-4-thiazolyl]methylthio]ethyl]-N'-(4-methyl-2-thiazolyl)urea, a compound according to claim 1.

3. N-[2[[5-[(dimethylamino)methyl]-2-furanyl]methylthio]ethyl]-N'-(4-methyl-2-thiazolyl)urea, a compound according to claim 1.

4. N-[2-[5-methyl-1H-imidazol-4-yl)methylthio]ethyl]-N'-(methyl-2-thiazolyl)urea; a compound according to claim 1.

* * * * *